(12) United States Patent
Zhang et al.

(10) Patent No.: US 8,766,011 B2
(45) Date of Patent: Jul. 1, 2014

(54) METHOD FOR SYNTHESIZING AMINOALCOHOLS

(75) Inventors: Yanshi Zhang, Shaker Heights, OH (US); Krishnan Tamareselvy, Brecksville, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 43 days.

(21) Appl. No.: 13/389,131

(22) PCT Filed: Aug. 5, 2010

(86) PCT No.: PCT/US2010/044533
§ 371 (c)(1),
(2), (4) Date: Feb. 6, 2012

(87) PCT Pub. No.: WO2011/017510
PCT Pub. Date: Feb. 10, 2011

(65) Prior Publication Data
US 2012/0136174 A1 May 31, 2012

Related U.S. Application Data

(60) Provisional application No. 61/231,780, filed on Aug. 6, 2009.

(51) Int. Cl.
*C07C 213/00* (2006.01)
(52) U.S. Cl.
USPC ........................................................ 564/503
(58) Field of Classification Search
USPC ........................................................ 564/503
See application file for complete search history.

(56) References Cited

U.S. PATENT DOCUMENTS 2,477,842 A * 8/1949 Wenner .......................... 544/170
2,618,658 A * 11/1952 Caldwell ........................ 564/473

OTHER PUBLICATIONS

Wilhelm Wenner, "Raney Nickel as Hydrogenation Catalyst in Acid Solutions, Preparation of Amino Alcohols from Mannich Bases", Journal of Organic Chemistry, American Chemical Society, vol. 15, No. 2, Mar. 1, 1950, pp. 301-304.
C. Mannich et al., "Beta-Methylamino-Alpha, Alpha-dimethylpropionaldehyde and the Alcohol Corresponding to it", Chemische Berichte, Verlag Chemie GmbH, Weinheim, DE, vol. 65, No. 3, Mar. 2, 1932, pp. 385-390.
Melvin S. Newman et al., "Investigation of the gem-Dialkyl Effect in Medicinal Agents", Journal of Medicinal Chemistry, American Chemical Society, Washington, US, vol. 15, No. 10, Oct. 1, 1972; pp. 1003-1006.

* cited by examiner

*Primary Examiner* — Brian J Davis
(74) *Attorney, Agent, or Firm* — Thoburn T. Dunlap

(57) ABSTRACT

The present invention relates to a method for synthesizing amonoalcohols (e.g., aminoalcohols that contain an amine group that is either unsubstituted, mono-substituted, or di-substituted) and to the products formed therefrom. In one embodiment, the present invention relates to a method for synthesizing aminoalcohols from a corresponding aminoaldehyde and to the products formed therefrom. In another embodiment, the present invention relates to a method for synthesizing aminoalcohols from a corresponding aminoaldehyde via a hydrogenation process using a suitable catalyst (e.g., Raney® Nickel) and to the products formed therefrom. In still another embodiment, the present invention relates to aminoalcohols formed via direct hydrogenation from a corresponding aminoaldehyde without the intervening step of converting the aminoaldehyde starting material to a salt.

19 Claims, 10 Drawing Sheets

METHOD FOR SYNTHESIZING AMINOALCOHOLS

CROSS REFERENCE TO RELATED APPLICATION

This application claims priority from PCT Application Serial No. PCT/US2010/044533 filed on Aug. 5, 2010, which claims the benefit of U.S. Provisional Application No. 61/231,780 filed on Aug. 6, 2009.

FIELD OF THE INVENTION

The present invention relates to a method for synthesizing aminoalcohols (e.g., aminoalcohols that contained an amine group that is either unsubstituted, mono-substituted, or di-substituted) and to the products formed therefrom. In one embodiment, the present invention relates to a method for synthesizing aminoalcohols from a corresponding aminoaldehyde and to the products formed therefrom. In another embodiment, the present invention relates to a method for synthesizing aminoalcohols from a corresponding aminoaldehyde via a hydrogenation process using a suitable catalyst (e.g., Raney® Nickel) and to the products formed therefrom. In still another embodiment, the present invention relates to aminoalcohols formed via direct hydrogenation from a corresponding free aminoaldehyde without the intervening step of converting the aminoaldehyde starting material to a salt.

BACKGROUND OF THE INVENTION

Various methods are used to synthesize aminoalcohols. However, they all suffer from the various drawbacks detailed below. The discussion of the various methods that are currently utilized to synthesize an aminoalcohol will utilize 3-dimethylamino-2,2-dimethyl-1-propanol (DMADMPOL) as an exemplary situation.

The first route known in the art is to reduce an ester or amide as is shown in the exemplary synthesis route shown below:

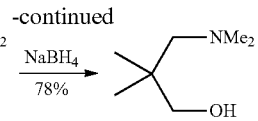

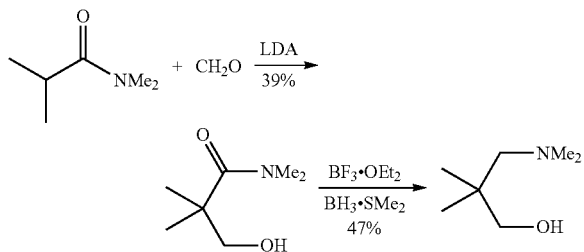

where LDA is lithium diisopropylamide $[(CH_3)_2CH]_2NLi$. This synthesis route is not practical due to the low yield and high cost of lithium reagent used in the system (see, e.g., Madder et al., J. Chem. Sci., Perkin Trans. 1997, 2, p. 2787).

The second route known in the art is to reduce a corresponding aldehyde as is shown in the exemplary synthesis routes shown below:

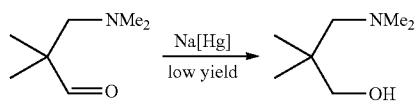

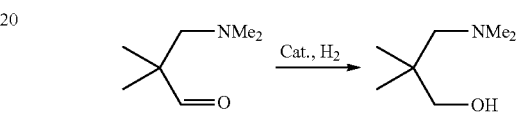

The above routes involve the reduction of 3-dimethylamino-2,2-dimethyl-propanal with a reducing agent such as Na[Hg] (see, e.g., Mannich et al., Ber., 1932, 65, p, 378) or NaBH$_4$ (see, e.g., Traynelis et al., J. J. Org. Chem., 1961, 26, pp. 686 to 691). These routes although possible, still require a large quantity of reducing agent in order to produce the desired aminoalcohol. Additionally, the yield on the first reduction route is too low to be practical.

A third route, which has been attempted, is to subject a corresponding aldehyde to hydrogenation with a catalyst as is shown in the exemplary synthesis route shown below:

However, various difficulties have been reported relating to the hydrogenation of this aldehyde shown above (see, e.g., W. Wenner, J. Org. Chem., 1950, 15, 2, pp. 301 to 304). As reported therein, the hydrogenation of DMADMPAL did not stop at the desired alcohol stage (see, e.g., W. Wenner, J. Org. Chem., 1950, 15, 2, pp. 301 to 304; Mannich et al., Ber., 1922, 55, pp. 356 to 365; and Mannich et al., Ber., 1932, 65, pp. 385 to 390).

It has also been reported that when hydrochloride salt of 3-dimethylamino-2,2-dimethyl-1-propanal (DMADMPAL) is hydrogenated with noble metal catalysts, only poor yields of the desired product 3-dimethylamino-2,2-dimethyl-1-propanol (DMADMPOL) are obtained. Part of the reason for such poor yields is that hydrogenolysis of the amine functional group is observed. Hydrogenation of the free amine gave even a worse result even though noble metal and nickel catalysts were tested (see, e.g., W. Wenner, J. Org. Chem., 1950, 15, 2, pp. 301 to 304). The hydrogenation of 3-dimethylamino-2,2-dimethyl-1-propanal (DMADMPAL) was finally achieved when the hydrochloride salt was employed in conjunction with Raney® Nickel as a catalyst (see, e.g., W. Wenner, J. Org. Chem., 1950, 15, 2, pp. 301 to 304 and U.S. Pat. No. 2,477,842). This process is also not cost efficient since protonation and deprotonation of the amine moiety of the aminoaldehyde added significant processing cost to the final product.

Regarding U.S. Pat. No. 2,477,842, this patent utilizes a method to convert an aminoaldehyde to an aminoalcohol that requires the use of an acid compound to convert the aminoaldehyde into a salt in order to achieve sufficient protonation of the amino group to permit the desired conversion. As would be apparent to those of skill in the art, the process of U.S. Pat. No. 2,477,842 is pH dependent and requires the use of a base compound at a later point to permit the reconversion of the salt compound to the desired aminoalcohol. Additional drawbacks of the process disclosed in U.S. Pat. No. 2,477,842 are: (i) the need to use at least stoichiometric amount (or even in excess of a stoichiometric amount) of acid to ensure complete protonation of the aminoaldehyde starting material to the necessary aminoaldehyde salt; and (ii) the need to use a stoichiometric amount (or even in excess of a stoichiometric amount) of base to neutralize the acid utilized in the reaction process and to permit the reconversion of the salt compound to the desired aminoalcohol.

Given the above, there is a need for a synthesis route for producing aminoalcohols from a suitable starting component (e.g., a free aminoaldehyde) that is both practical and permits the realization of suitably high yield without the need for the intermediate steps of protonating the amine moiety of the aminoaldehyde starting material and the subsequent deprotonation of the amine moiety of the aminoalcohol reaction product to recover the free aminoalcohol.

SUMMARY OF THE INVENTION

The present invention relates to a method for synthesizing aminoalcohols (e.g., aminoalcohols that contained an amine group that is either unsubstituted, mono-substituted, or di-substituted) and to the products formed therefrom. In one embodiment, the present invention relates to a method for synthesizing aminoalcohols from a corresponding aminoaldehyde and to the products formed therefrom. In another embodiment, the present invention relates to a method for synthesizing aminoalcohols from a corresponding aminoaldehyde via a hydrogenation process using a suitable catalyst (e.g., Raney® Nickel) and to the products formed therefrom. In still another embodiment, the present invention relates to aminoalcohols formed via direct hydrogenation from a corresponding aminoaldehyde without the intervening step of converting the aminoaldehyde starting material to a salt.

By free aminoaldehyde is meant that the amine moiety present on the aminoaldehyde compound is in its free state (i.e., not protonated or neutralized). The aminoaldehyde compound used in the reaction as the starting reactant is not a salt. By free aminoalcohol is meant that the amine moiety present on the aminoalcohol is in its free state (i.e., not protonated or neutralized). The aminoalcohol product synthesized in the reaction is not a salt.

The reactions, reactants, compositions and products of the present invention may suitably comprise, consist of, or consist essentially of the components, elements, and process delineations described herein. The invention illustratively disclosed herein suitably may be practiced in the absence of any element which is not specifically disclosed herein.

In one embodiment, the present invention relates to a method for producing an aminoalcohol from an aminoaldehyde, the method comprising the steps of: (i) subjecting an aminoaldehyde according to Formula (I) below to a hydrogenation reaction by combining the aminoaldehyde with hydrogen and a catalyst to yield a corresponding aminoalcohol:

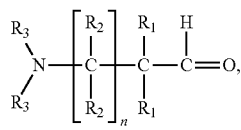
(I)

where each $R_1$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_1$ substituents and the carbon atom to which they are attached can form a saturated or unsaturated $C_3$ to $C_{20}$ cyclic group, heterocyclic group or carbocyclic group; where each $R_2$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_2$ substituents and the carbon atom to which they are attached can form a saturated or unsaturated $C_3$ to $C_{20}$ cyclic group, heterocyclic group or carbocyclic group; where one $R_1$ substituent and one $R_2$ substituent and the carbon atoms to which they are attached can form a saturated $C_3$ to $C_{20}$ cyclic group or a saturated $C_3$ to $C_{20}$ heterocyclic group, wherein the remaining $R_1$ substituent and $R_2$ substituent either form a second cyclic structure as defined above or wherein the remaining $R_1$ substituent and $R_2$ substituent are individually substituted with a group listed above; where each $R_3$ is independently selected from hydrogen, linear or branched $C_1$ to $C_{30}$ alkyl groups, linear or branched $C_1$ to $C_{30}$ alkyl groups that contain one or more heteroatoms, linear or branched $C_2$ to $C_{30}$ alkenyl groups, linear or branched $C_2$ to $C_{30}$ alkenyl groups that contain one or more heteroatoms, linear or branched $C_2$ to $C_{30}$ alkynyl groups, linear or branched $C_2$ to $C_{30}$ alkynyl groups that contain one or more heteroatoms, $C_4$ to $C_{20}$ aryl groups, $C_4$ to $C_{20}$ aryl groups that contain one or more heteroatoms, $C_4$ to $C_{20}$ cycloalkyl groups, $C_4$ to $C_{20}$ cycloalkyl groups that contain one or more heteroatoms, $C_4$ to $C_{20}$ heterocyclic groups, or where both $R_3$ substituents and the nitrogen atom to which they are attached can form a saturated or unsaturated $C_2$ to $C_{20}$ heterocyclic group or a saturated or unsaturated $C_2$ to $C_{20}$ heterocyclic group having two or more heteroatoms; and where n is equal to an integer in the range of 1 to about 30; and (ii) collecting the aminoalcohol.

In another embodiment, the present invention relates to a method for producing an aminoalcohol from a partially neutralized aminoaldehyde, the method comprising the steps of: (A) combining an aminoaldehyde according to Formula (I) below with less than a stoichiometric amount of an acid to form a partially neutralized aminoaldehyde composition.

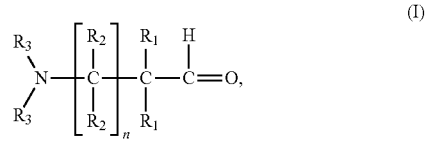
(I)

where each $R_1$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_1$ substituents and the carbon atom to which they are attached can form a saturated or unsaturated $C_3$ to $C_{20}$ cyclic group, heterocyclic group or carbocyclic group; where each $R_2$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_2$ substituents and the carbon atom to which they are attached can form a saturated or unsaturated $C_3$ to $C_{20}$ cyclic group, heterocyclic group or carbocyclic group; where one $R_1$ substituent and one $R_2$ substituent and the carbon atoms to which they are attached can form a saturated $C_3$ to $C_{20}$ cyclic group or a saturated $C_3$ to $C_{20}$ heterocyclic group, wherein the remaining $R_1$ substituent and $R_2$ substituent either form a second cyclic structure as defined above or wherein the remaining $R_1$ substituent and $R_2$ substituent are individually substituted with a group listed above; where each $R_3$ is independently selected from hydrogen, linear or branched $C_1$ to $C_{30}$ alkyl groups, linear or branched $C_1$ to $C_{30}$ alkyl groups that contain one or more heteroatoms, linear or branched $C_2$ to $C_{30}$ alkenyl groups, linear or branched $C_2$ to $C_{30}$ alkenyl groups that contain one or more heteroatoms, linear or branched $C_2$ to $C_{30}$ alkynyl groups, linear or branched $C_2$ to $C_{30}$ alkynyl groups that contain one or more heteroatoms, $C_4$ to $C_{20}$ aryl groups, $C_4$ to $C_{20}$ aryl groups that contain one or more heteroatoms, $C_4$ to $C_{20}$ cycloalkyl groups, $C_4$ to $C_{20}$ cycloalkyl groups that contain one or more heteroatoms, $C_4$ to $C_{20}$ heterocyclic groups, or where both $R_3$ substituents and the nitrogen atom to which they are attached can form a saturated or unsaturated $C_2$ to $C_{20}$ heterocyclic group or a saturated or unsaturated $C_2$ to $C_{20}$ heterocyclic group having two or more heteroatoms; and where n is equal to an integer in the range of 1 to about 30; and (B) subjecting the aminoaldehyde salt to a hydrogenation reaction by combining the aminoaldehyde salt with hydrogen and a catalyst to yield a corresponding aminoalcohol; and (C) collecting the aminoalcohol, wherein the amount of acid utilized in Step (A) is less than about 0.9 molar equivalents for every 1 equivalent of aminoaldehyde.

DETAILED DESCRIPTION OF THE INVENTION

Figure 1:
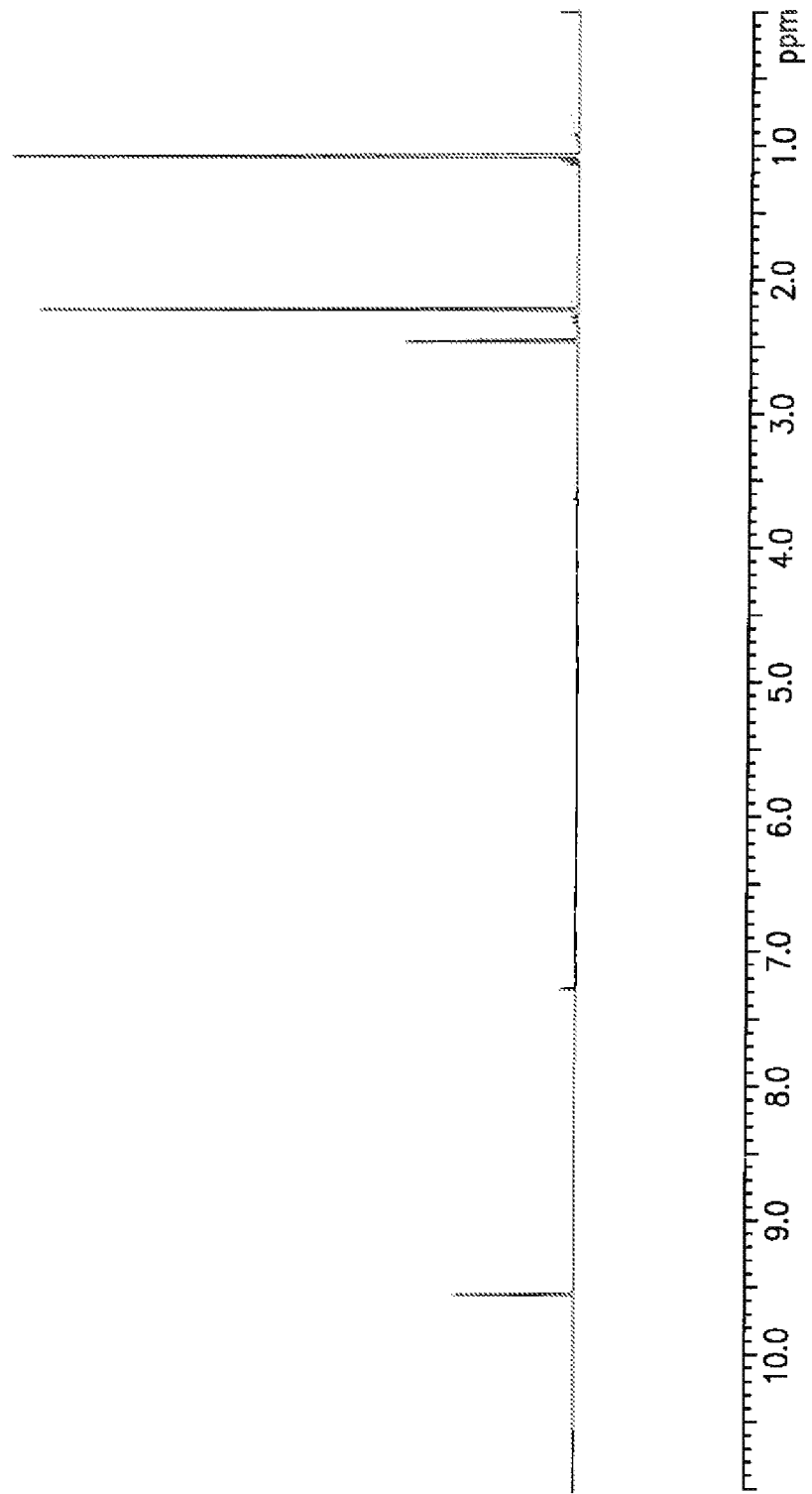
FIG. 1 is a 500 mHz $^1$H NMR spectra of crude 3-dimethylamino-2,2-dimethyl-1-propanal (DMADMPAL)

The present invention relates to a method for synthesizing aminoalcohols (e.g., aminoalcohols that contained an amine group that is either unsubstituted, mono-substituted, or di-substituted) and to the products formed therefrom. In one embodiment, the present invention relates to a method for synthesizing aminoalcohols from a corresponding aminoaldehyde and to the products formed therefrom. In another embodiment, the present invention relates to a method for synthesizing aminoalcohols from a corresponding aminoaldehyde via a hydrogenation process using a suitable catalyst (e.g., Raney® Nickel) and to the products formed therefrom. In still another embodiment, the present invention relates to aminoalcohols formed via direct hydrogenation from a corresponding aminoaldehyde without the intervening step of converting the aminoaldehyde starting material to a salt.

In one embodiment the present invention relates to aminoalcohols formed from a corresponding aminoaldehyde via hydrogenation using a Raney® Nickel catalyst.

In one embodiment, the aminoaldehyde is selected from those represented by Formula (I):

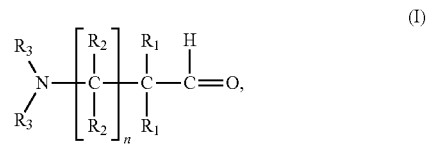

where each $R_1$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, where the heteroatoms are selected from a carbonyl group, N, S, P, or O, or linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, where the heteroatoms, if present, are selected from a carbonyl group, N, S, P, or O; where each $R_2$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, where the heteroatoms are selected from a carbonyl group, N, S, P, or O, or linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, where the heteroatoms, if present, are selected from a carbonyl group, N, S, P, or O; where n is equal to an integer in the range of 1 to about 30; and where each $R_3$ is independently selected from hydrogen, linear or branched $C_1$ to $C_{30}$ alkyl groups, linear or branched $C_2$ to $C_{30}$ alkenyl groups, linear or branched $C_2$ to $C_{30}$ alkynyl groups, $C_3$ to $C_{20}$ aryl groups, $C_3$ to $C_{20}$ cycloalkyl groups or $C_2$ to $C_{20}$ heterocyclic groups, where the heteroatoms, if present, are selected from a carbonyl group, N, S, P, or O.

In another embodiment, both $R_1$ substituents and the carbon atom to which they are attached can form a saturated or unsaturated $C_3$ to $C_{20}$ cyclic group, heterocyclic group or carbocyclic group, where the heteroatoms, if present, are selected from a carbonyl group, N, S, P, or O. In another embodiment, both $R_2$ substituents and the carbon atom to which they are attached can form a saturated or unsaturated $C_3$ to $C_{20}$ cyclic group, heterocyclic group or carbocyclic group, where the heteroatoms, if present, are selected from a carbonyl group, N, S, P, or O. In still another embodiment, one $R_1$ substituent and one $R_2$ substituent and the carbon atoms to which they are attached can form a saturated $C_3$ to $C_{20}$ cyclic group or a saturated $C_3$ to $C_{20}$ heterocyclic group, where the heteroatoms, if present, are selected from a carbonyl group, N, S, P, or O. In this embodiment, the remaining $R_1$ substituent and one $R_2$ substituent can either form a second cyclic structure as defined above or the remaining $R_1$ substituent and $R_2$ substituent are individually substituted with a group listed above.

In another embodiment, each $R_3$ is independently selected from hydrogen, linear or branched $C_1$ to $C_{30}$ alkyl groups that contain one or more heteroatoms (e.g., a carbonyl group, N, S, P, or O), linear or branched $C_2$ to $C_{30}$ alkenyl groups that contain one or more heteroatoms (e.g., a carbonyl group, N, S, P, or O), linear or branched $C_2$ to $C_{30}$ alkynyl groups that contain one or more heteroatoms (e.g., a carbonyl group, N, S, P, or O), $C_4$ to $C_{20}$ aryl groups that contain one or more heteroatoms (e.g., a carbonyl group, N, S, P, or O), $C_4$ to $C_{20}$ cycloalkyl groups that contain one or more heteroatoms (e.g., a carbonyl group, N, S, P, or O). In still another embodiment, both $R_3$ substituents and the nitrogen atom to which they are attached can form a substituted or unsubstituted, saturated or unsaturated $C_2$ to $C_{20}$ heterocyclic group, or a substituted or unsubstituted, saturated or unsaturated $C_2$ to $C_{20}$ heterocyclic group having two or more heteroatoms (and substituted heteroatoms) including the above-mentioned bridging nitrogen atom where the one or more additional heteroatoms and substituted heteroatoms are selected from a carbonyl group, NH, $NC(O)CH_3$, $NC(O)CH_2CH_3$, N, S, P, or O. When substituted said heterocyclic groups are substituted by one or more substituents selected from $C_1$ to $C_{10}$ alkyl, $C_6$ to $C_{12}$ aryl, and carboxyl. Here, as well as else where in the specification and claims, individual numerical values (including carbon atom numerical values), or limits, can be combined to form additional non-disclosed and/or non-stated ranges.

In still another embodiment, each $R_1$ is independently selected from hydrogen, linear or branched $C_3$ to $C_{15}$ alkyl groups, $C_4$ to $C_{10}$ cycloalkyl groups, saturated $C_3$ to $C_{10}$ heterocyclic groups, where the heteroatoms are selected from a carbonyl group, N, S, P, or O, or linear or branched $C_3$ to $C_{15}$ alkyl groups that can contain one or more of, or any mixture thereof, either $C_4$ to $C_{10}$ cycloalkyl groups or saturated $C_3$ to $C_{10}$ heterocyclic groups, where the heteroatoms, if present, are selected from a carbonyl group, N, S, P, or O; each $R_2$ is independently selected from hydrogen, linear or branched $C_3$ to $C_{15}$ alkyl groups, $C_4$ to $C_{10}$ cycloalkyl groups, saturated $C_3$ to $C_{10}$ heterocyclic groups, where the heteroatoms are selected from a carbonyl group, N, S, P, or O, or linear or branched $C_3$ to $C_{15}$ alkyl groups that can contain one or more of, or any mixture thereof, either $C_4$ to $C_{10}$ cycloalkyl groups or saturated $C_3$ to $C_{10}$ heterocyclic groups, where the heteroatoms, if present, are selected from a carbonyl group, N, S, P, or O; and each $R_3$ is independently selected from hydrogen, linear or branched $C_3$ to $C_{15}$ alkyl groups, linear or branched $C_4$ to $C_{20}$ alkenyl groups, linear or branched $C_4$ to $C_{20}$ alkynyl groups, $C_4$ to $C_{10}$ aryl groups, $C_4$ to $C_{10}$ cycloalkyl groups or $C_3$ to $C_{10}$ heterocyclic groups, where the heteroatoms, if present, are selected from a carbonyl group, N, S, P, or O.

In still another embodiment, both $R_1$ substituents and the carbon atom to which they are attached can form a saturated or unsaturated $C_4$ to $C_{10}$ cyclic group, heterocyclic group or carbocyclic group, where the heteroatoms, if present, are selected from a carbonyl group, N, S, P, or O. In still another embodiment, both $R_2$ substituents and the carbon atom to which they are attached can form a saturated or unsaturated $C_4$ to $C_{10}$ cyclic group, heterocyclic group or carbocyclic group, where the heteroatoms, if present, are selected from a carbonyl group, N, S, P, or O. In still another embodiment, one $R_1$ substituent and one $R_2$ substituent and the carbon atoms to which they are attached can form a saturated $C_4$ to $C_{10}$ cyclic group or a saturated $C_4$ to $C_{10}$ heterocyclic group, where the heteroatoms, if present, are selected from a carbonyl group, N, S, P, or O. In this embodiment, the remaining $R_1$ substituent and one $R_2$ substituent can either form a second cyclic structure as defined above or the remaining $R_1$ substituent and $R_2$ substituent are individually substituted with a group listed above.

In still another embodiment, each $R_3$ is independently selected from hydrogen, linear or branched $C_3$ to $C_{15}$ alkyl groups that contain one or more heteroatoms (e.g., a carbonyl group, N, S, P, or O), linear or branched $C_4$ to $C_{20}$ alkenyl groups that contain one or more heteroatoms (e.g., a carbonyl group, N, S, P, or O), linear or branched $C_4$ to $C_{20}$ alkynyl groups that contain one or more heteroatoms (e.g., a carbonyl group, N, S, P, or O), $C_5$ to $C_{10}$ aryl groups that contain one or more heteroatoms (e.g., a carbonyl group, N, S, P, or O), $C_5$ to $C_{10}$ cycloalkyl groups that contain one or more heteroatoms (e.g., a carbonyl group, N, S, P, or O). In still another embodiment, both $R_3$ substituents and the nitrogen atom to which they are attached can form a substituted or unsubstituted, saturated or unsaturated $C_3$ to $C_{10}$ heterocyclic group, or a substituted or unsubstituted, saturated or unsaturated $C_3$ to $C_{10}$ heterocyclic group having two or more heteroatoms (and substituted heteroatoms) including the above-mentioned bridging nitrogen atom where the one or more additional heteroatoms and substituted heteroatoms are selected from a carbonyl group, NH, $NC(O)CH_3$, $NC(O)CH_2CH_3$, N, S, P, or O. When substituted said heterocyclic groups are substituted by one or more substituents selected from $C_1$ to $C_{10}$ alkyl, $C_6$ to $C_{12}$ aryl, and carboxyl. Here, as well as else where in the specification and claims, individual numerical values (including carbon atom numerical values), or limits, can be combined to form additional non-disclosed and/or non-stated ranges.

In still another embodiment, each $R_1$ is independently selected from hydrogen, linear or branched $C_5$ to $C_8$ alkyl groups, $C_5$ to $C_8$ cycloalkyl groups, saturated $C_4$ to $C_8$ heterocyclic groups, where the heteroatoms are selected from a carbonyl group, N, S, P, or O, or linear or branched $C_5$ to $C_8$ alkyl groups that can contain one or more of, or any mixture thereof, either $C_5$ to $C_8$ cycloalkyl groups or saturated $C_4$ to $C_8$ heterocyclic groups, where the heteroatoms, if present, are selected from a carbonyl group, N, S, P, or O; each $R_2$ is independently selected from hydrogen, linear or branched $C_5$ to $C_8$ alkyl groups, $C_5$ to $C_8$ cycloalkyl groups, saturated $C_4$ to $C_8$ heterocyclic groups, where the heteroatoms are selected from a carbonyl group, N, S, P, or O, or linear or branched $C_5$ to $C_8$ alkyl groups that can contain one or more of, or any mixture thereof, either $C_5$ to $C_8$ cycloalkyl groups or saturated $C_4$ to $C_8$ heterocyclic groups, where the heteroatoms, if present, are selected from a carbonyl group, N, S, P, or O; and each $R_3$ is independently selected from hydrogen, linear or branched $C_5$ to $C_8$ alkyl groups, linear or branched $C_6$ to $C_{10}$ alkenyl groups, linear or branched $C_6$ to $C_{10}$ alkynyl groups, $C_5$ to $C_8$ aryl groups, $C_5$ to $C_8$ cycloalkyl groups or $C_4$ to $C_8$ heterocyclic groups, where the heteroatoms, if present, are selected from a carbonyl group, N, S, P, or O.

In still another embodiment, both $R_1$ substituents and the carbon atom to which they are attached can form a saturated or unsaturated $C_5$ to $C_8$ cyclic group, heterocyclic group or carbocyclic group, where the heteroatoms, if present, are selected from a carbonyl group, N, S, P, or O. In still another embodiment, both $R_2$ substituents and the carbon atom to which they are attached can form a saturated or unsaturated $C_5$ to $C_8$ cyclic group, heterocyclic group or carbocyclic group, where the heteroatoms, if present, are selected from a carbonyl group, N, S, P, or O. In still another embodiment, one $R_1$ substituent and one $R_2$ substituent and the carbon atoms to which they are attached can form a saturated $C_5$ to $C_8$ cyclic group or a saturated $C_5$ to $C_8$ heterocyclic group, where the heteroatoms, if present, are selected from a carbonyl group, N, S, P, or O. In this embodiment, the remaining $R_1$ substituent and one $R_2$ substituent can either form a second cyclic structure as defined above or the remaining $R_1$ substituent and $R_2$ substituent are individually substituted with a group listed above.

In still another embodiment, each $R_3$ is independently selected from hydrogen, linear or branched $C_5$ to $C_8$ alkyl groups that contain one or more heteroatoms (e.g., a carbonyl group, N, S, P, or O), linear or branched $C_6$ to $C_{10}$ alkenyl groups that contain one or more heteroatoms (e.g., a carbonyl group, N, S, P, or O), linear or branched $C_6$ to $C_{10}$ alkynyl groups that contain one or more heteroatoms (e.g., a carbonyl group, N, S, P, or O), $C_5$ to $C_8$ aryl groups that contain one or more heteroatoms (e.g., a carbonyl group, N, S, P, or O), $C_5$ to $C_8$ cycloalkyl groups that contain one or more heteroatoms (e.g., a carbonyl group, N, S, P, or O). In still another embodiment, both $R_3$ substituents and the nitrogen atom to which they are attached can form a substituted or unsubstituted, saturated or unsaturated $C_4$ to $C_8$ heterocyclic group, or a substituted or unsubstituted, saturated or unsaturated $C_4$ to $C_8$ heterocyclic group having two or more heteroatoms (and substituted heteroatoms) including the above-mentioned bridging nitrogen atom where the one or more additional heteroatoms and substituted heteroatoms are selected from a carbonyl group, NH, $NC(O)CH_3$, $NC(O)OCH_3$, $NC(O)OCH_2CH_3$, N, S, P, or O. When substituted said heterocyclic groups are substituted with one or more substituents selected from $C_1$ to $C_{10}$ alkyl, $C_6$ to $C_{12}$ aryl, and carboxyl. Here, as well as else where in the specification and claims, individual numerical values (including carbon atom numerical values), or limits, can be combined to form additional non-disclosed and/or non-stated ranges.

In still another embodiment, each $R_1$ is independently selected from hydrogen, or linear or branched $C_1$ to $C_6$ alkyl groups; each $R_2$ is independently selected from hydrogen, or linear or branched $C_1$ to $C_6$ alkyl groups, n is equal to an integer in the range of 1 to about 20; and each $R_3$ is independently selected from hydrogen, linear or branched $C_1$ to $C_{15}$ alkyl groups, linear or branched $C_2$ to $C_{15}$ alkenyl groups, linear or branched $C_2$ to $C_{15}$ alkynyl groups, $C_4$ to $C_{10}$ aryl groups, $C_4$ to $C_{10}$ cycloalkyl groups or $C_4$ to $C_{10}$ heterocyclic groups. In another embodiment, each $R_3$ is independently selected from hydrogen, linear or branched $C_1$ to $C_{15}$ alkyl groups that contain one or more heteroatoms (e.g., a carbonyl group, N, S, P, or O), linear or branched $C_2$ to $C_{15}$ alkenyl groups that contain one or more heteroatoms (e.g., a carbonyl group, N, S, P, or O), linear or branched $C_2$ to $C_{15}$ alkynyl groups that contain one or more heteroatoms (e.g., a carbonyl group, N, S, P, or O), $C_4$ to $C_{10}$ aryl groups that contain one or more heteroatoms (e.g., a carbonyl group, N, S, P, or O), $C_4$ to $C_{10}$ cycloalkyl groups that contain one or more heteroatoms (e.g., a carbonyl group, N, S, P, or O).

In still another embodiment, both $R_1$ substituents and the carbon atom to which they are attached can form a saturated or unsaturated $C_4$ to $C_6$ cyclic group, heterocyclic group or carbocyclic group, where the heteroatoms, if present, are selected from a carbonyl group, N, S, P, or O. In still another embodiment, both $R_2$ substituents and the carbon atom to which they are attached can form a saturated or unsaturated $C_4$ to $C_6$ cyclic group, heterocyclic group or carbocyclic group, where the heteroatoms, if present, are selected from a carbonyl group, N, S, P, or O. In still another embodiment, both $R_3$ substituents and the nitrogen atom to which they are attached can form a substituted or unsubstituted, saturated or unsaturated $C_4$ to $C_6$ heterocyclic group, or a substituted or unsubstituted, saturated or unsaturated $C_4$ to $C_6$ heterocyclic group having two or more heteroatoms (and substituted heteroatoms) including the above-mentioned bridging nitrogen atom where the one or more additional heteroatoms and substituted heteroatoms are selected from a carbonyl group, NH, $NC(O)CH_3$, $NC(O)CH_2CH_3$, N, S, P, or O. In still yet another embodiment, n is equal to an integer in the range of about 2 to about 15, or even an integer in the range of about 4 to about 10. Here, as well as else where in the specification and claims, individual numerical values (including carbon atom numerical values), or limits, can be combined to form additional non-disclosed and/or non-stated ranges.

In still yet another embodiment, each $R_1$ is a methyl group, each $R_2$ is a hydrogen; each $R_3$ is selected from a hydrogen, linear or branched $C_1$ to $C_8$ alkyl groups; and wherein n is equal to an integer from 1 to 5.

In one embodiment, the above "starting" aminoaldehydes for conversion to a corresponding aminoalcohols are produced via synthesis routes known to those of skill in the art (see, e.g., U.S. Pat. Nos. 2,477,842 and 1,824,676, both of which are incorporated herein for their teachings of synthesis routes for producing aminoaldehydes). In another embodiment, the following exemplary synthesis route can be utilized to produce the desired aminoaldehyde "starting" material. It should be noted that the following synthesis route for an aminoaldehyde is exemplary in nature and the present invention is not limited thereto.

In one embodiment, 3-dimethylamino-2,2-dimethyl-1-propanal (DMADMPAL) is synthesized according to the following reaction route:

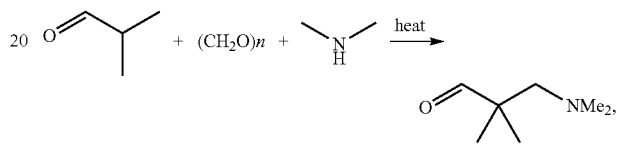

where n is an integer in the range of 1 to about 100, or from 2 to about 50, or from about 4 to about 25, or even from about 8 to about 15. Here, as well as else where in the specification and claims, individual numerical values (including carbon atom numerical values), or limits, can be combined to form additional non-disclosed and/or non-stated ranges. In another embodiment, n is equal to 1 (i.e., formaldehyde) or n is equal to 8 (a paraformaldehyde). In still another embodiment, paraformaldehyde is utilized regardless of the number of repeating units (i.e., n can be of any suitable value and is not limited to the ranges noted above).

Figure 2:
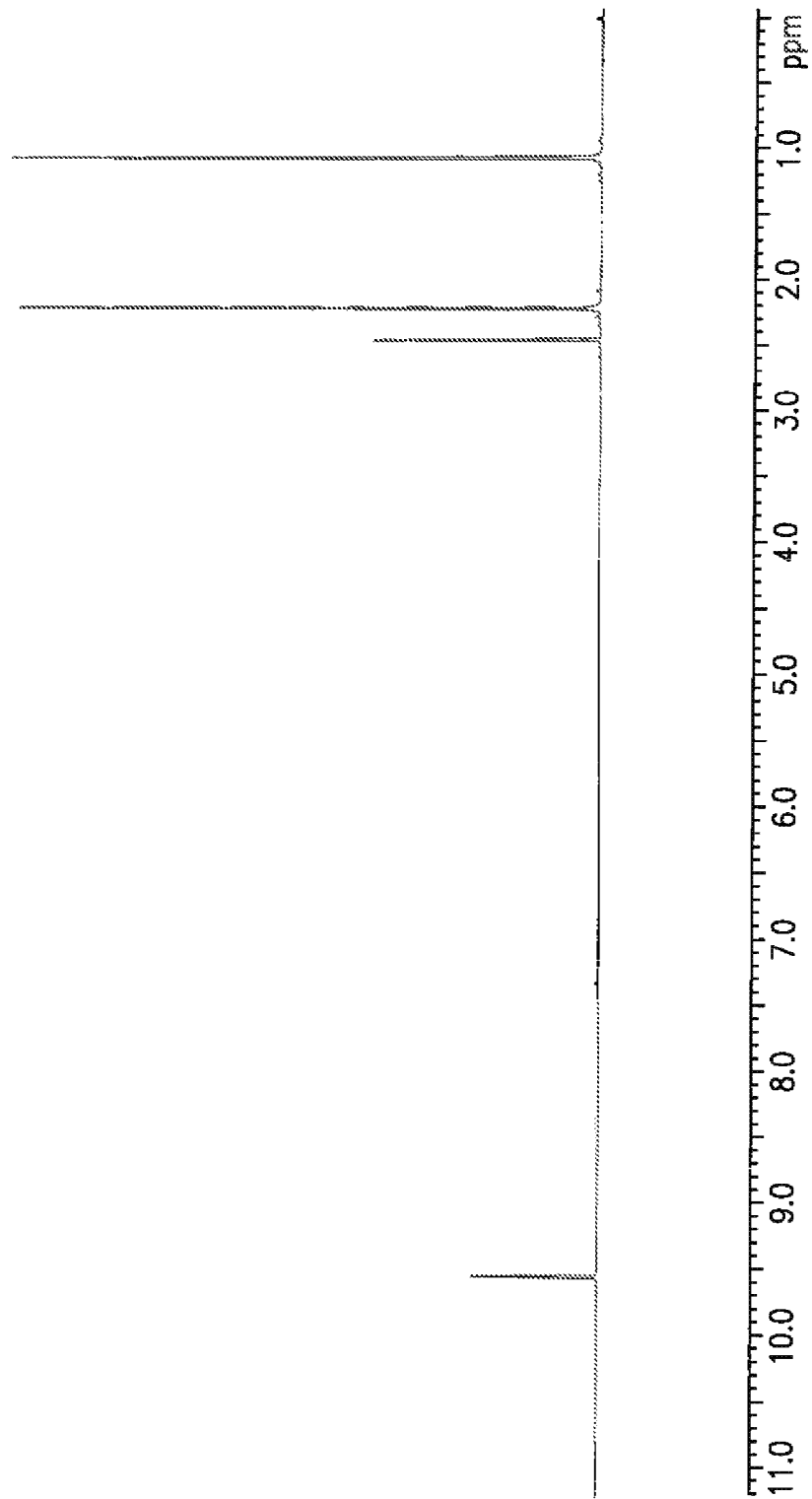
FIG. 2 is a 500 mHz $^1$H NMR spectra of distilled 3-dimethylamino-2,2-dimethyl-1-propanal (DMADMPAL)
Figure 3:
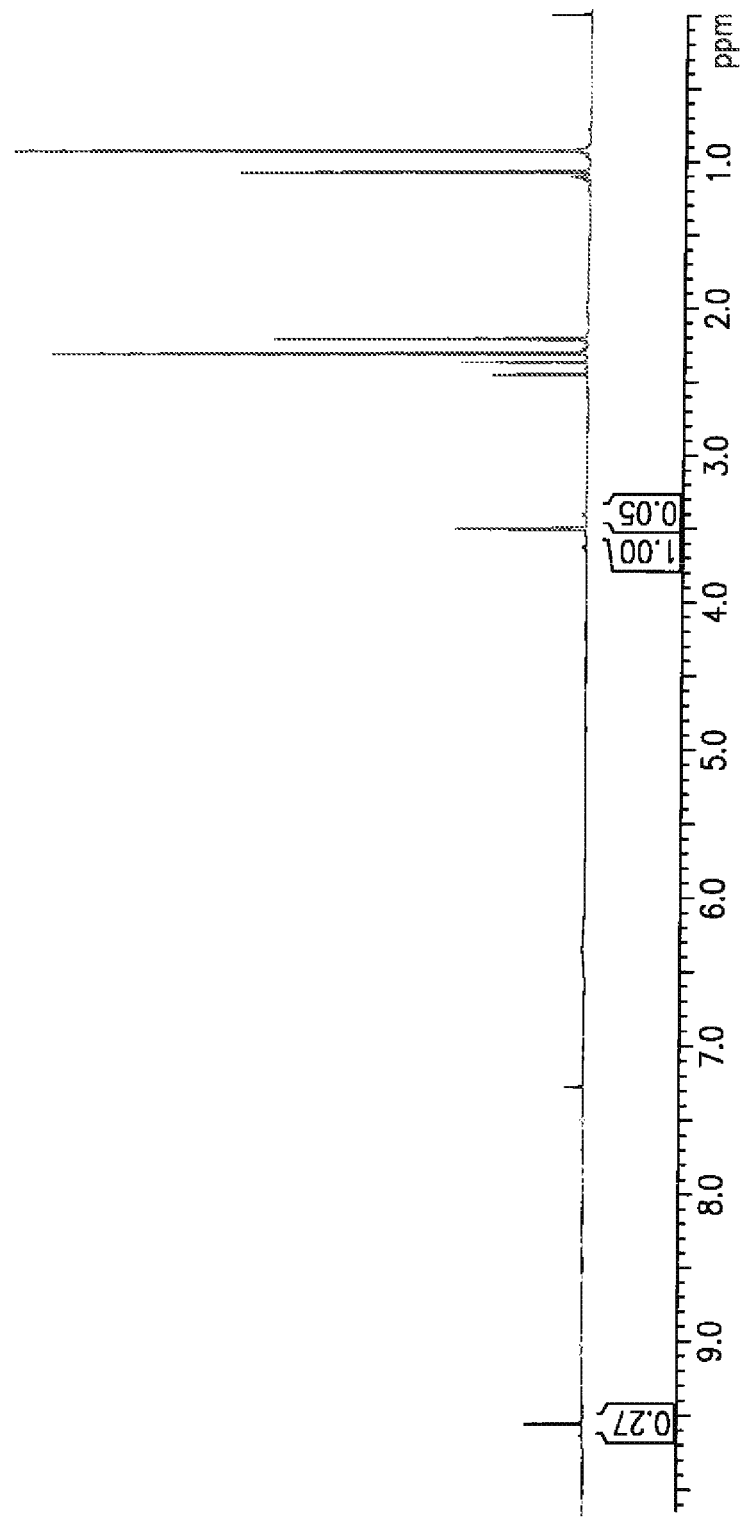
FIG. 3 is a 500 mHz $^1$H NMR spectra of Comparative Example 1.
Figure 4:
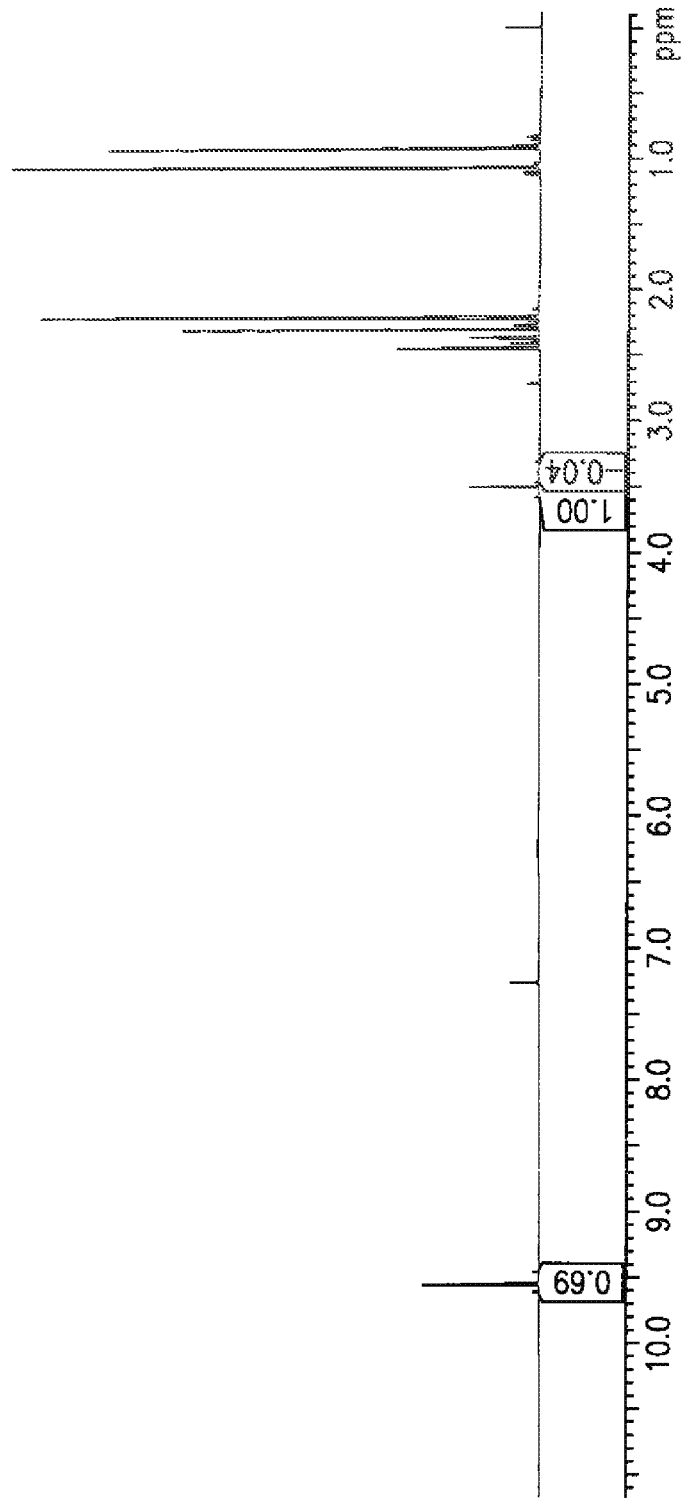
FIG. 4 is a 500 mHz $^1$H NMR spectra of Comparative Example 2.
Figure 5:
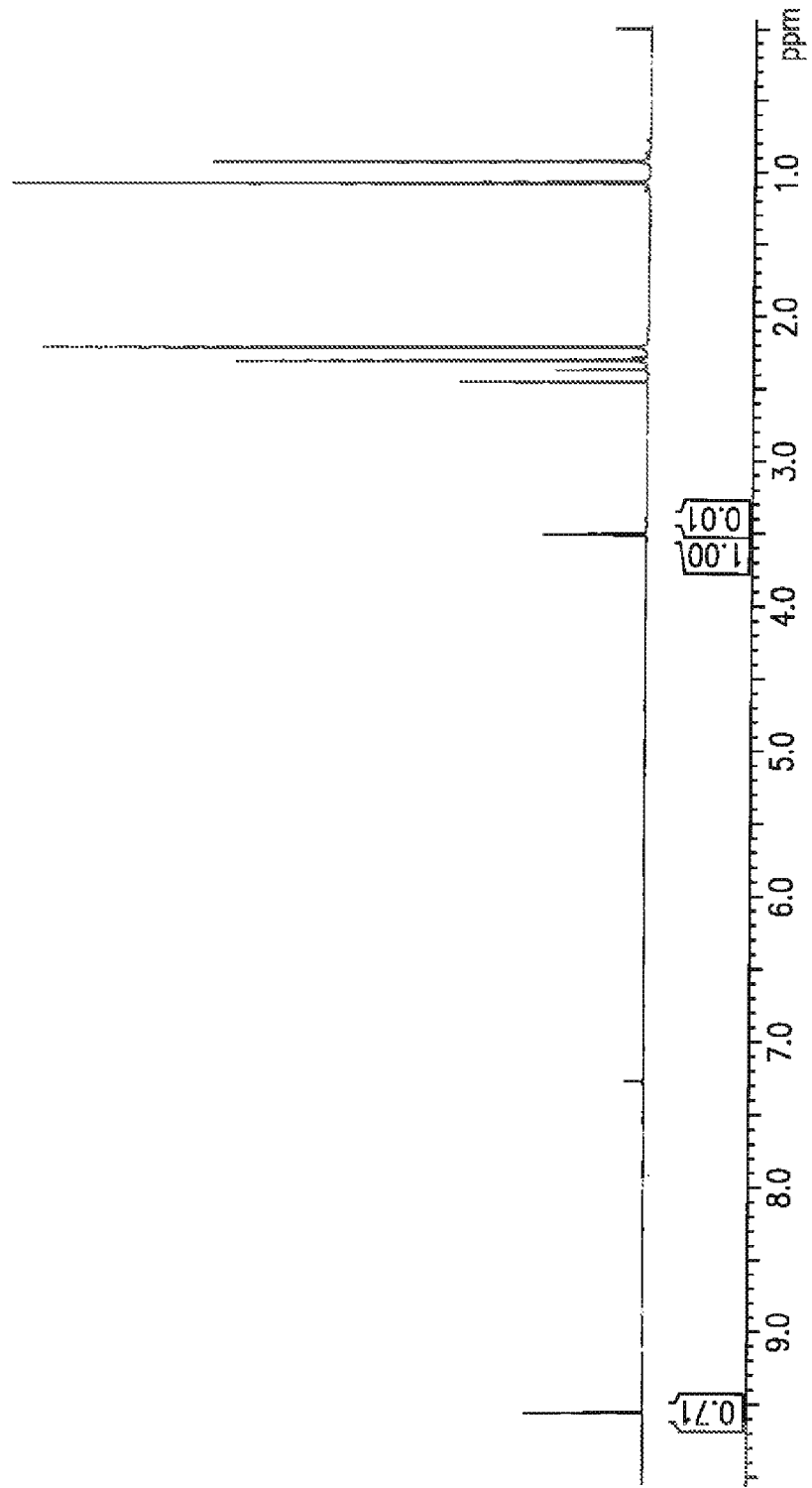
FIG. 5 is a 500 mHz $^1$H NMR spectra of Comparative Example 3.
Figure 6:
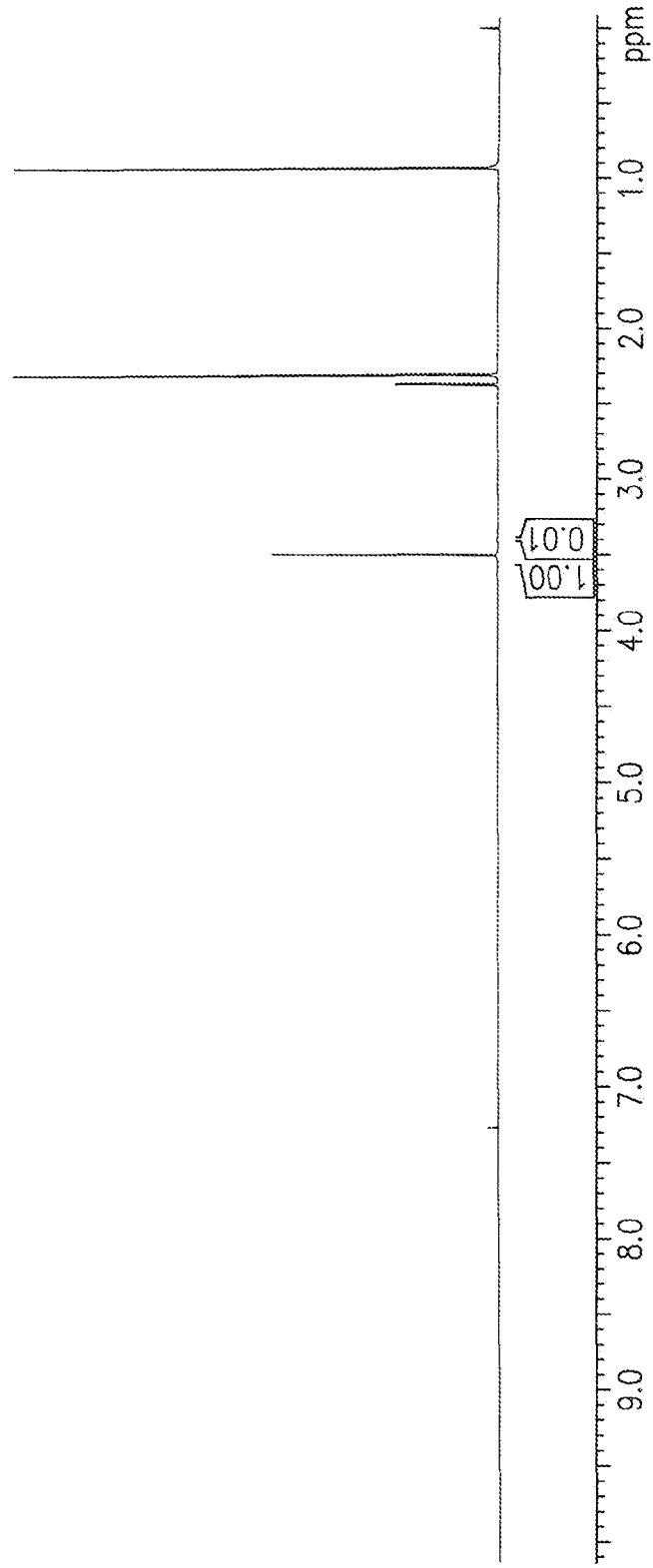
FIG. 6 is a 500 mHz $^1$H NMR spectra of Experimental Example 1.
Figure 7:
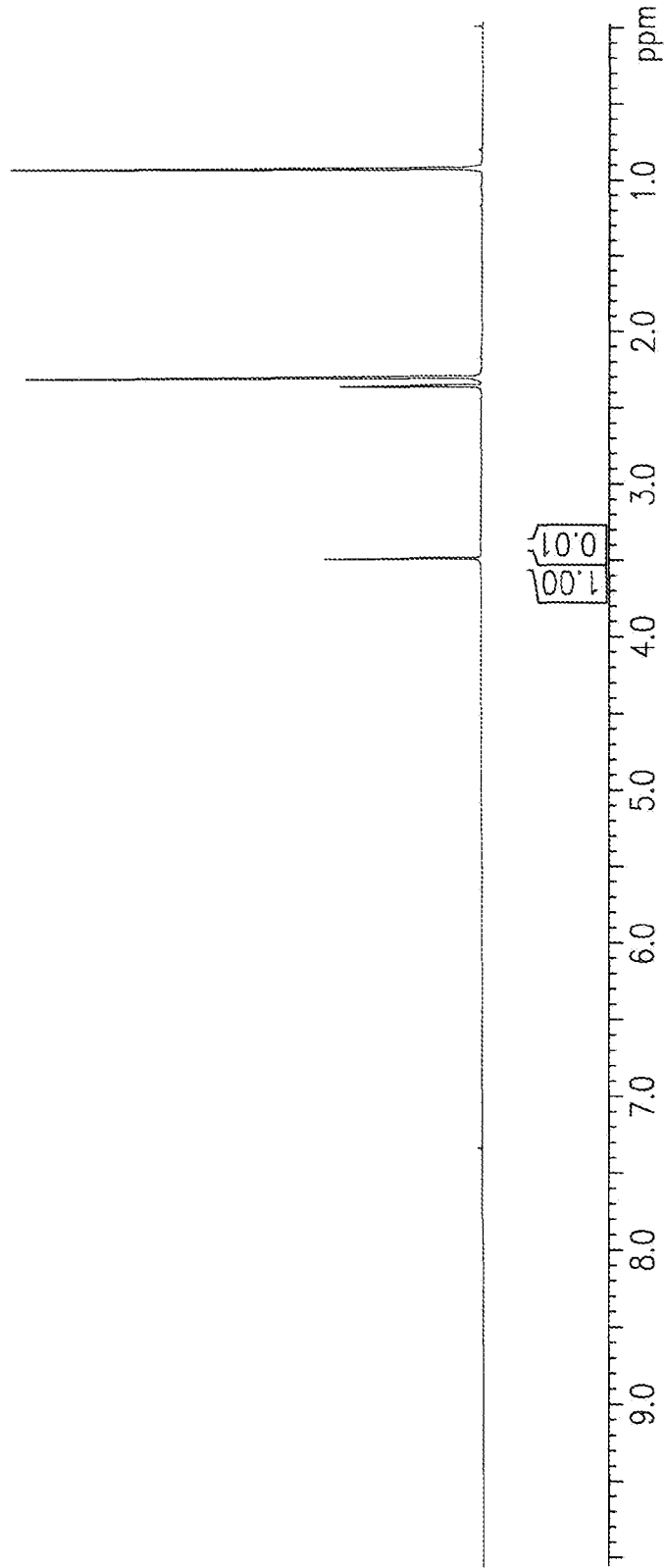
FIG. 7 is a 500 mHz $^1$H NMR spectra of Experimental Example 2.
Figure 8:
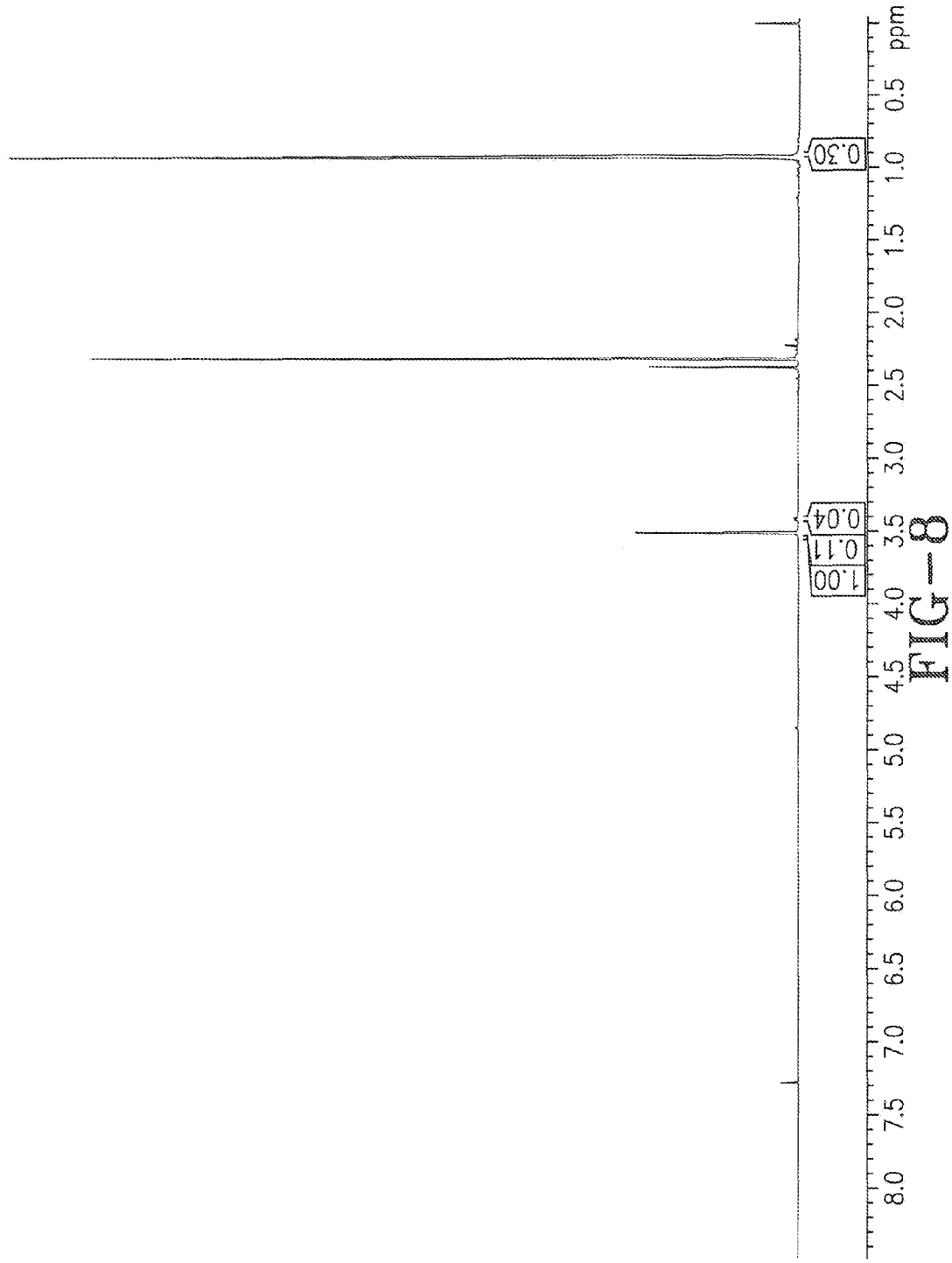
FIG. 8 is a 500 mHz $^1$H NMR spectra of Experimental Example 3.
Figure 9:
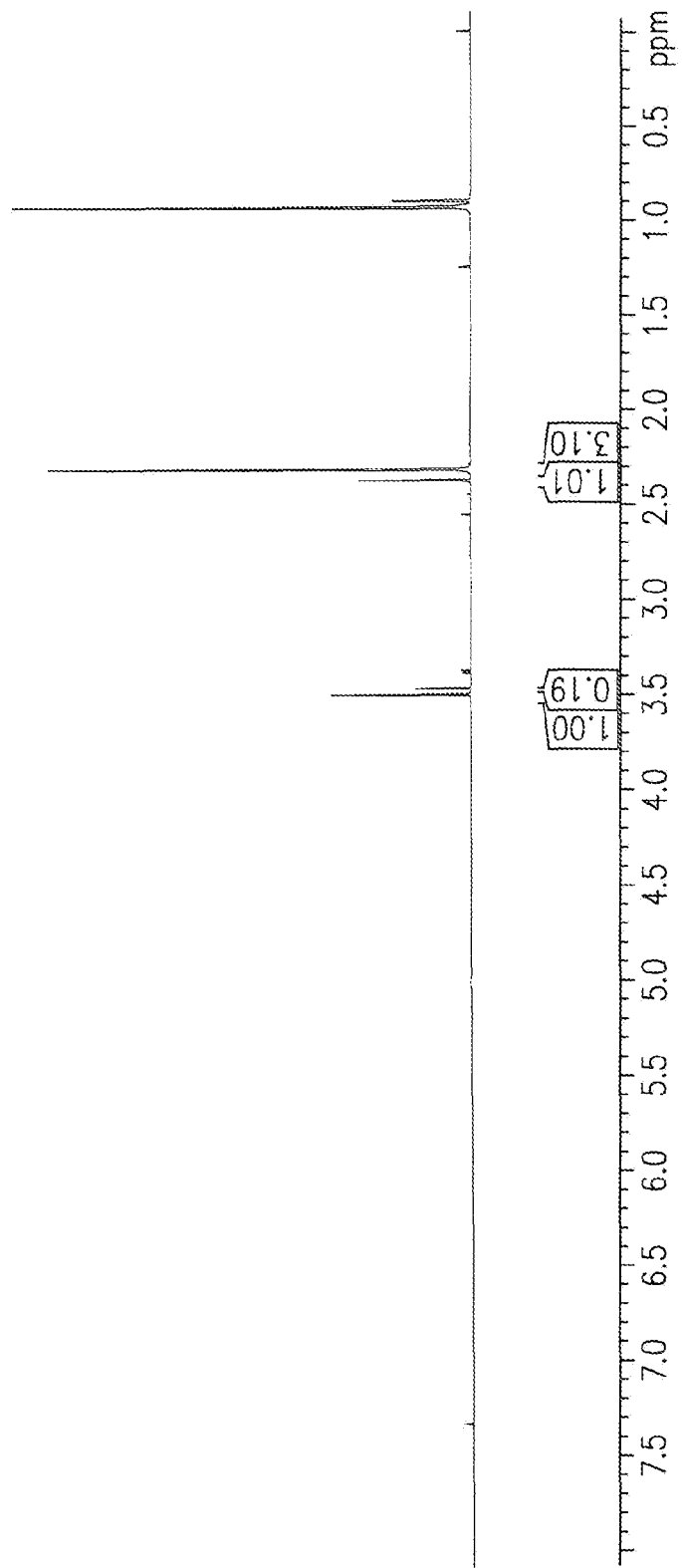
FIG. 9 is a 500 mHz $^1$H NMR spectra of Experimental Example 4.
Figure 10:
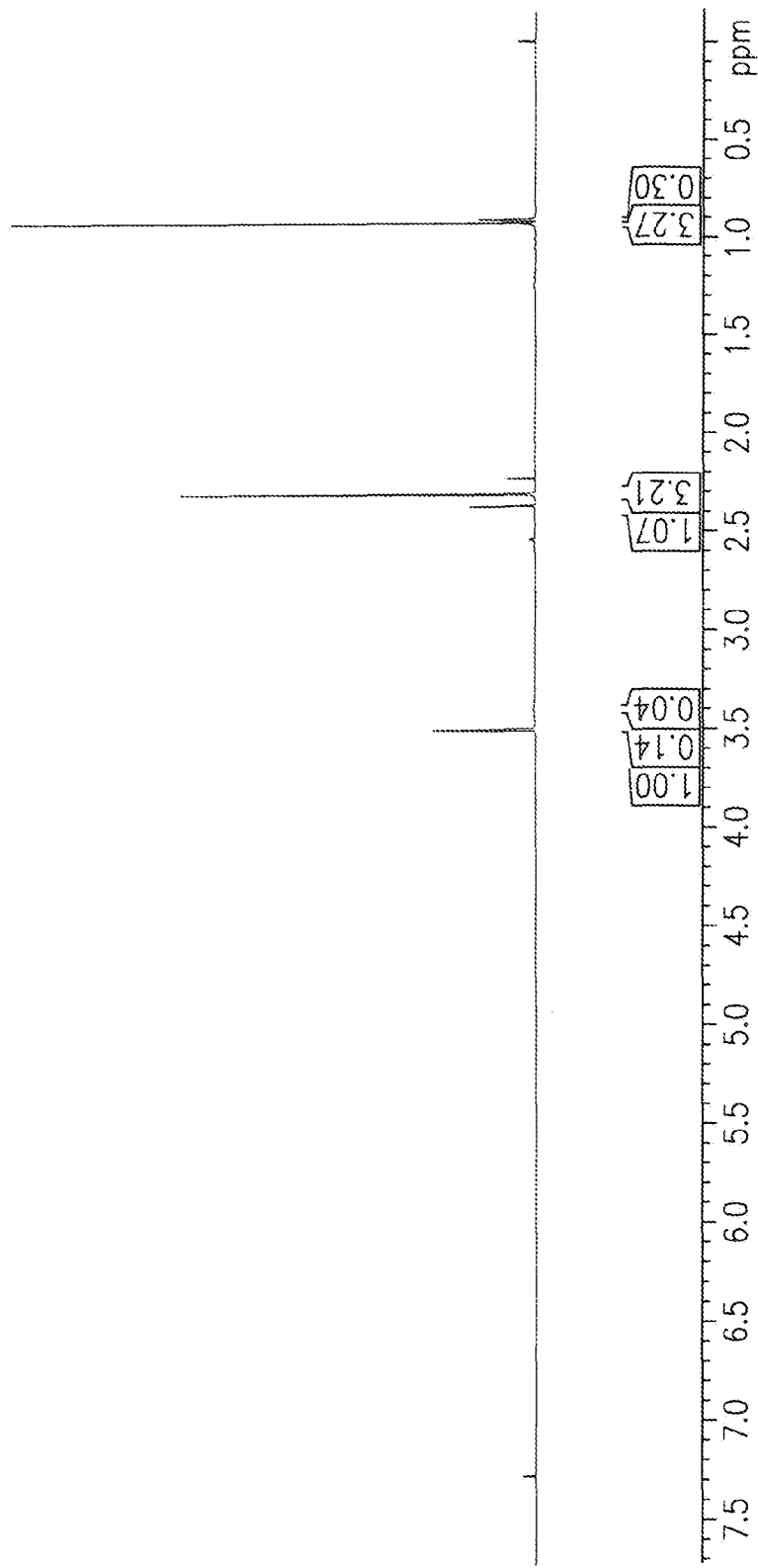
FIG. 10 is a 500 mHz $^1$H NMR spectra of Experimental Example 5.

In one particular synthesis embodiment, the DMADMPAL starting material is formed from isobutyraldehyde (144 grams, 2 moles), paraformaldehyde (97%—63 grams, 2 moles), and dimethylamine solution (40% —226 grams, 2 moles). The crude product, DMADMPAL which is a yellow to light brown liquid. The crude product has good purity as can be seen from the $^1$H NMR spectra of FIG. 1. The crude DMADMPAL product can be further purified by vacuum distillation to yield a colorless liquid. FIG. 2 is a $^1$H NMR spectra of the purified DMADMPAL product.

As discussed above, the present invention relates to a method for synthesizing aminoalcohols from a corresponding aminoaldehyde and to the products formed therefrom. In another embodiment, the present invention relates to a method for synthesizing aminoalcohols from a corresponding free aminoaldehyde via a hydrogenation process using a suitable catalyst (e.g., a metal hydrogenation catalyst or a binary metal hydrogenation catalyst) and to the free aminoalcohol product formed therefrom. In one embodiment, the hydrogenation catalyst of the present invention is selected from any suitable hydrogenation catalyst that contain, or are based on, one or more transition metals including, but not limited to, Ni, Pd, Pt, Cu, Ag, Au, Cr, Mo, Fe, Ru, Rh, Re, Zn, Cd, Hg, Al, or suitable combinations of two or more thereof. In another embodiment, the hydrogenation catalyst of the present invention can be one or more metals, one or more metal oxide compounds, one or more metal salt compounds, or a suitable combination of two or more thereof, where the one or more metal is selected from Ni, Pd, Pt, Cu, Ag, Au, Cr, Mo, Fe, Ru, Rh, Re, Zn, Cd, Hg or Al. In still another embodiment, the present invention can utilize any type of hydrogenation catalyst that are designed to be used in conjunction with nitrogen-containing reactants. It will be appreciated that in this embodiment, the hydrogenation catalyst that is utilized in conjunction with the present invention should selectively hydrogenate the aldehyde functionality without hydrogenating the nitrogen atom of the aminoaldehyde starting material.

In still another embodiment, the hydrogenation catalysts utilized in conjunction with the present invention are binary metal hydrogenation catalysts. Such catalysts include, but are not limited to, nickel-aluminum (Ni—Al) binary catalysts. Nickel-aluminum binary catalysts are also referred to in the art as nickel-aluminum skeletal catalysts and nickel-aluminum sponge-metal catalysts. In one aspect, the preparation of nickel-aluminum binary catalysts involves alloying about 50 parts nickel with about 50 parts aluminum by pyro-metallurgical techniques as described in U.S. Pat. Nos. 1,628,190 and 1,915,473, pulverizing the nickel-aluminum alloy and then dissolving away most of the aluminum with an aqueous sodium hydroxide solution [J. Am. Chem. Soc. 54, 4116 (1932)] to give a porous substrate. The porous nickel-aluminum is then washed to remove any residual sodium hydroxide [Ind. and Eng. Chem. 33 1199 (1940)]. The ratio of nickel to aluminum used in the alloy can range from about 1 to about 4.

In one instance, the method of the present invention involves the controlled hydrogenation of a desired aminoaldehyde in accordance with Formula (I) above via a hydrogenation reaction using a suitable catalyst. In one embodiment, the catalyst is a nickel-aluminum binary metal catalyst such as Raney® Nickel and is commercially available from, for example, W.R. Grace & Co., Pfaltz & Bauer or Sigma-Aldrich. Nickel-aluminum binary metal catalysts also are commercially available from Johnson Matthey Catalysts under the Sponge Metal™ trade name. However, the present invention is not limited thereto. In one instance, the controlled synthesis route for a desired aminoalcohol utilizes a free aminoaldehyde and is as shown below in Reaction Scheme 1:

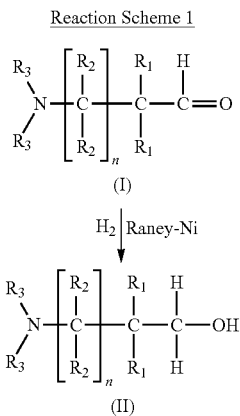

where each $R_1$, $R_2$ and $R_3$ are independently selected from the groups defined above; and where n is defined as above. In one embodiment, any suitable amount of hydrogenation catalyst can be utilized in conjunction with Reaction Scheme 1 including, but not limited to, amounts in excess of a weight equivalent based on the amount of aminoaldehyde starting material. In one embodiment of Reaction Scheme 1, the ratio of aminoaldehyde to catalyst is controlled so that about 1 weight equivalent of aminoaldehyde is reacted with about 0.0001 to about 0.8 weight equivalents of catalyst. In another embodiment, the ratio of aminoaldehyde to catalyst is controlled so that about 1 weight equivalent of aminoaldehyde is reacted with about 0.001 to about 0.75 weight equivalents of catalyst. In still another embodiment, the ratio of aminoaldehyde to catalyst is controlled so that about 1 weight equivalent of aminoaldehyde is reacted with about 0.1 to about 0.5 weight equivalents of catalyst. Here, as well as else where in the specification and claims, individual numerical values (including, if applicable, carbon atom numerical values), or limits, can be combined to form additional non-disclosed and/or non-stated ranges.

In one embodiment, Reaction Scheme 1 is conducted at a pressure in the range of about 1 psi to about 10,000 psi, or from about 10 psi to about 5,000 psi, or from about 50 psi to about 1,000 psi, or even from about 250 psi to about 750 psi. In one embodiment, Reaction Scheme 1 is conducted at a temperature of about 0° C. to about 300° C., or from about 15° C. to about 250° C., or from about 25° C. to about 200° C., or even from about 30° C. to about 150° C. Here, as well as else where in the specification and claims, individual numerical values (including, if applicable, carbon atom numerical values), or limits, can be combined to form additional non-disclosed and/or non-stated ranges.

In another embodiment, the controlled synthesis route for a desired aminoalcohol utilizes an aminoaldehyde composition wherein only a portion of the amine moieties on the aminoaldehyde in the composition are protonated (neutralized with an acid). The aminoaldehyde salt is formed in accordance with Reaction Scheme 2:

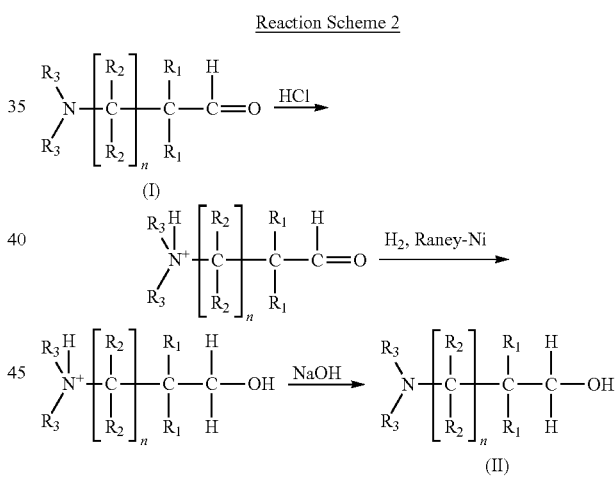

where each $R_1$, $R_2$ and $R_3$ are independently selected from the groups defined above; and where n is defined as above. In one embodiment of Reaction Scheme 2, the conversion of the free aminoaldehyde to the corresponding aminoaldehyde salt is controlled by utilizing less than about 0.9 molar equivalents of a suitable acid (e.g., HCl) for every 1 molar equivalent of free aminoaldehyde. In another embodiment, the conversion of the free aminoaldehyde to the corresponding aminoaldehyde salt is controlled by utilizing less than about 0.8 molar equivalents, less than about 0.75 molar equivalents, less than about 0.6 molar equivalents, less than about 0.5 molar equivalents, less than about 0.4 molar equivalents, less than about 0.3 molar equivalents, less than about 0.2 molar equivalents, or even less than about 0.1 molar equivalents of acid (e.g., HCl) for every 1 molar equivalent of free aminoaldehyde. In still another embodiment, no acid is utilized and instead the free aminoaldehyde is converted to the desired free aminoalcohol without conversion to the corresponding aminoaldehyde salt. As would be apparent to those of skill in the art, when no acid (i.e., zero molar equivalents of acid) are utilized the reaction proceeds according to Reaction Scheme 1 above rather then Reaction Scheme 2. Here, as well as else where in the specification and claims, individual numerical values (including, if applicable, carbon atom numerical values), or limits, can be combined to form additional non-disclosed and/or non-stated ranges.

In one aspect of Reaction Scheme 2, the aminoaldehyde starting material is neutralized to less than a 90% degree of neutralization, less than 80% in another aspect, less than 75% in a further aspect, and less than 60%, 50%, 40%, 30%, 20%, and 10% in a still further aspect of the invention.

In one embodiment, any suitable amount of hydrogenation catalyst can be utilized in conjunction with Reaction Scheme 2 including, but not limited to, amounts in excess of a weight equivalent based on either: (a) the amount of the free aminoaldehyde starting material present, (b) the amount of the corresponding aminoaldehyde salt present; or (c) the amount of both the free aminoaldehyde starting material present and the corresponding aminoaldehyde salt present. In one embodiment of the above hydrogenation reaction, the ratio of either (a), (b) or (c), as described above, to catalyst is controlled so that about 1 weight equivalent of aminoaldehyde is reacted with about 0.0001 to about 0.8 weight equivalents of catalyst. In another embodiment, the ratio of either (a), (b) or (c), as described above, to catalyst is controlled so that about 1 weight equivalent of aminoaldehyde is reacted with about 0.001 to about 0.75 weight equivalents of catalyst. In still another embodiment, the ratio of either (a), (b) or (c), as described above, to catalyst is controlled so that about 1 weight equivalent of aminoaldehyde is reacted with about 0.1 to about 0.5 weight equivalents of catalyst. Here, as well as else where in the specification and claims, individual numerical values (including, if applicable, carbon atom numerical values), or limits, can be combined to form additional non-disclosed and/or non-stated ranges.

It should be noted that although Reaction Scheme 2 above utilizes hydrochloric acid, the present invention is not limited thereto. Rather, any suitable acid compound can be utilized to form the intermediate aminoaldehyde salt compound shown in Reaction Scheme 2. In one embodiment, various inorganic and organic acids can be utilized in conjunction with Reaction Scheme 2. Exemplary inorganic acids include, but are not limited to, hydrochloric acid, nitric acid, sulfuric acid, sulfamic acid, phosphoric acid, or suitable mixtures of two or more thereof. Exemplary organic acids include, but are not limited to, formic acid, acetic acid, citric acid, salicylic acid, lactic acid, glycolic acid, or suitable mixtures of two or more thereof. In still another embodiment, any suitable mixture of one or more inorganic acids in combination with one or more organic acids can be utilized in Reaction Scheme 2.

Regarding the base neutralization step of Reaction Scheme 2, this portion of the reaction is shown schematically as reactions of this type are known to those of skill in the art. It should be noted that although Reaction Scheme 2 above exemplifies sodium hydroxide, the present invention is not limited thereto. Rather, any suitable alkaline pH adjusting agent and/or base compound can be utilized to "reconvert" the intermediate aminoalcohol salt compound of Reaction Scheme 2 to the desired aminoalcohol. In one embodiment, various inorganic and organic alkaline pH adjusting agents and/or bases can be utilized in conjunction with Reaction Scheme 2. Exemplary inorganic alkaline pH adjusting agents and/or bases include, but are not limited to, alkali metal hydroxides (e.g., sodium hydroxide and potassium hydroxide), ammonium hydroxide, alkali metal salts of inorganic acids (e.g., sodium borate (i.e., borax), sodium phosphate, sodium pyrophosphate, or suitable mixtures of two or more thereof.

Exemplary organic alkaline pH adjusting agents and/or bases include, but are not limited to, triethanolamine, diisopropylamine, dodecylamine, diisopropanolamine, aminomethyl propanol, cocamine, oleamine, morpholine, triamylamine, triethylamine, tromethamine(2-amino-2-hydroxymethyl)-1, 3-propanediol), tetrakis(hydroxy propyl)ethylenediamine, or suitable mixtures of two or more thereof. In still another embodiment, any suitable mixture of one or more inorganic alkaline pH adjusting agents and/or bases in combination with one or more organic alkaline pH adjusting agents and/or bases can be utilized in Reaction Scheme 2.

In one embodiment, Reaction Scheme 2 is conducted at a pressure in the range of about 1 psi to about 10,000 psi, or from about 10 psi to about 5,000 psi, or from about 50 psi to about 1,000 psi, or even from about 250 psi to about 750 psi. In one embodiment, Reaction Scheme 2 is conducted at a temperature of about 0° C. to about 300° C., or from about 15° C. to about 250° C., or from about 25° C. to about 200° C., or even from about 30° C. to about 150° C. Here, as well as else where in the specification and claims, individual numerical values (including, if applicable, carbon atom numerical values), or limits, can be combined to form additional non-disclosed and/or non-stated ranges.

Regarding any of the embodiments covered by Reaction Schemes 1 and/or 2, such reactions can be run as neat reactions. As used herein, a neat reaction is one that has less than about 10 percent by weight of one or more extraneous and/or added solvents. In another embodiment, a neat reaction is one that has less than about 7.5 percent by weight of one or more extraneous and/or added solvents, less than about 5 percent by weight of one or more extraneous and/or added solvents, less than about 2.5 percent by weight of one or more extraneous and/or added solvents, less than about 1 percent by weight of one or more extraneous and/or added solvents, less than about 0.5 percent by weight of one or more extraneous and/or added solvents, less than about 0.1 percent by weight of one or more extraneous and/or added solvents, or even no amount of one or more extraneous and/or added solvents (i.e., has zero additional solvents, or is free from additional solvents). Here, as well as else where in the specification and claims, individual numerical values (including, if applicable, carbon atom numerical values), or limits, can be combined to form additional non-disclosed and/or non-stated ranges.

In the embodiments where one or more extraneous and/or added solvents are present in a neat reaction, the weight amount of the one or more extraneous and/or added solvents is based on the total weight of the reactants utilized in either Reaction Scheme 1 and/or 2 illustrated above. In the embodiment where Reaction Schemes 1 and/or 2 are free from the one or more extraneous and/or added solvents (i.e., has zero additional solvents), the reactants utilized in Reaction Schemes 1 and/or 2 provide the necessary reaction media for each of the above Reaction Schemes to proceed as illustrated.

In still another embodiment, Reaction Schemes 1 and/or 2 can be run in a solvent. In this embodiment, the amount of solvent utilized in conjunction with any of the embodiments of Reaction Schemes 1 and/or 2 can be less than about 95 percent by weight solvent, less than about 90 percent by weight solvent, less than about 80 percent by weight solvent, less than about 75 percent by weight solvent, less than about 70 percent by weight solvent, less than about 65 percent by weight solvent, less than about 60 percent by weight solvent, less than about 55 percent by weight solvent, less than about 50 percent by weight solvent, less than about 45 percent by weight solvent, less than about 40 percent by weight solvent, less than about 35 percent by weight solvent, less than about 30 percent by weight solvent, less than about 25 percent by weight solvent, less than about 20 percent by weight solvent, less than about 15 percent by weight solvent, or even less than about 12.5 percent by weight solvent. Here, as well as else where in the specification and claims, individual numerical values (including, if applicable, carbon atom numerical values), or limits, can be combined to form additional non-disclosed and/or non-stated ranges. In still another embodiment, any amount of solvent, including in excess of 100 percent by weight, can be utilized in conjunction with Reaction Schemes 1 and/or 2. In the embodiments where Reaction Schemes 1 and/or 2 are conducted in combination with one or more solvents, the weight amount of the one or more solvents is based on the total weight of the reactants utilized in either Reaction Scheme 1 and/or 2 illustrated above.

Suitable solvents for use in the present invention include, but are not limited to, one or more polar solvents, one or more non-polar solvents, or any suitable mixture of one or more polar solvents with one or more non-polar solvents. Exemplary polar solvents include, but are not limited to, water, $C_1$ to $C_8$ linear or branched alcohols (e.g., methanol, ethanol, propanol, iso-propanol, 1-butanol, 2-butanol, iso-butanol, tert-butanol, 1-pentanol, 2-pentanol, 3-pentanol, 1-hexanol, 2-hexanol, or 3-hexanol), N,N-dimethylformamide, N,N-dimethylacetamide, dimethyl sulfone, dimethyl sulfoxide, diphenyl sulfone, N-methylpyrrolidone, polar cyclic ethers (e.g., tetrahydrofuran, 2-methyltetrahydrofuran, or 3-methyltetrahydrofuran), or suitable mixtures of two or more thereof. Exemplary non-polar solvents include, but are not limited to, $C_5$ to $C_{12}$ linear or branched alkanes (e.g., pentane, hexane, heptane, or octane), non-polar aromatic hydrocarbons (e.g., benzene, toluene, or xylene), non-polar aliphatic esters (e.g., methyl acetate or ethyl acetate), non-polar chlorinated aliphatic and aromatic hydrocarbons (e.g., dichloromethane, chloroform, dichloroethane, chlorobenzene, or dichlorobenzenes), non-polar dialkyl ethers (e.g., diethyl ether, dipropyl ether, dibutyl ether, butyl ethyl ether, sec-butyl ethyl ether, tert-butyl ethyl ether, butyl methyl ether, sec-butyl methyl ether, or tert-butyl methyl ether), or suitable mixtures of two or more thereof. In one embodiment, where a mixture of polar/non-polar solvents are utilized the amount of one or more polar solvents to the one or more non-polar solvents can fall any where in the weight ratio range of about 99:1 to 1:99.

As is noted above, one embodiment of the present invention relates to the synthesis of DMADMPOL through hydrogenation of DMADMPAL using Raney® Nickel as catalyst. Both the hydrochloride salt form (i.e., the protonated variety, which is designated as P) and the free amine form (i.e., the reaction scheme that eliminates the use of an acid compound, which is designated as F) of DMADMPAL are utilized as "starting" materials. Again, the present invention is not limited to just the use of DMADMPAL as a starting material. Rather, the "starting" material of the present invention can be any compound according to Formula (I) as described above. The results of various Examples are listed in Table 1. The crude products are analyzed by $^1$H NMR, and representative peaks of major components of the crude products are integrated and listed.

TABLE 1

| | | | Major Peak's Integration | | |
|---|---|---|---|---|---|
| | | | DMADMPOL | Unreacted and/or Impurities Peaks | |
| Example | Form | pH | 3.5 ppm* | 9.53 ppm | 3.4 ppm |
| Comparative 1 | P | 1 to 2 | 100 | 27 | 5 |
| Comparative 2 | P | 6 to 7 | 100 | 69 | 4 |
| Comparative 3 | P | 3 to 4 | 100 | 71 | 1 |
| Experimental 1 | F | | 100 | 0 | 1 |
| Experimental 2 | F | | 100 | 0 | 1 |

*3.5 ppm peak is assigned an arbitrary value of 100 for comparison sake

The $^1$H NMR spectra of Comparative Examples 1 through 3 and Experimental Examples 1 and 2 are shown in FIGS. 3 through 7, respectively. The hydrogenation of hydrochloride salt form of DMADMPAL does not achieve the same yields as the hydrogenation of free DMADMPAL. The conversions for Comparative Examples 1 through 3 are lower, which can be evidenced by the presence of significant amount of aldehyde peak at 9.53 ppm. However, the hydrogenations of the salt form of DMADMPAL shows good selectivity as the by-product peak at 3.4 ppm is relatively minimal compared to the product peak at 3.5 ppm. As can be determined from the 1H NMR data, the conversion of the aminoaldehyde starting material to the desired aminoalcohol is not stoichiometric. While not wishing to be bound to any one numerical value, the conversion yield of the aminoaldehyde starting material to the desired aminoalcohol using the afore-mentioned hydrochloride salt intermediate is believed to be in the range of about 60 to 70 percent.

On the other hand, the hydrogenation of free DMADMPAL achieves an almost stoichiometric conversion. This can be seen from the data relating to Experimental Examples 1 and 2 in Table 1. Such data illustrates a clear absence of aldehyde peak at 9.53 ppm. When distilled DMADMPAL is employed, the reactions achieve about a 100% conversion, while the selectivity is about 99% according to the integrations. The by-product peak at 3.4 ppm is minimal. Thus, the present invention permits, in this embodiment, the achievement of a successful hydrogenation of free DMADMPAL which was not believed to be possible to those of skill in the art.

In another embodiment, the present invention makes possible the hydrogenation of crude free DMADMPAL. This reaction method is also successful with the DMADMPOL produced from the hydrogenation of crude free DMADMPAL yielding a purity of about 90%. The crude DMADMPOL product can, in another embodiment, be distilled to afford a final product purity of at least about 98%. As a result, it is advantageous in some instances to employ crude DMADMPAL for hydrogenation to avoid decomposition loss during distillation. High purity DMADMPOL can be obtained through distillation after the above-mentioned hydrogenation reaction is complete. In light of the above, the present invention encompasses the use of a "crude" free aminoaldehyde as a starting material to form a corresponding aminoalcohol via the above free reaction route.

Exemplary Procedure for the Hydrogenation of Hydrochloride Salt of DMADMPAL

Comparative Examples 1, 2 and 3

To a pressure vessel is charged DMADMPAL (1.0 equivalent), 6N HCl (1.01 to 1.04 equivalents). The pH value of the solution is adjusted to the desired value by means of the addition of ammonium hydroxide. To this solution is added a Raney® Nickel slurry available from Sigma-Aldrich, catalog number 510033 (W.R. Grace and Co. Raney® 2400, slurry in $H_2O$, active catalyst). The amount of catalyst utilized is about 5 to about 100 weight percent relative to the amount of DMADMPAL. The vessel is closed, and flushed with $H_2$ for about 5 minutes while stirring. The pressure in the vessel is increased to a pressure in the range of about 100 psi to about 1,000 psi, and then heated to a temperature in the range of about 30° C. to about 150° C. The heating is continued for about 3 hours. The reaction is then cooled to room temperature (e.g., about 21° C.), and the pressure is released before the vessel is flushed with $N_2$ for about 10 minutes. The resulting solution is then filtered. The solution is made strongly basic with NaOH, and organic portion is extracted out by the addition of a base or salt. The crude organic solution is analyzed by $^1$H NMR.

Exemplary Procedure for the Hydrogenation of Free Distilled DMADMPAL

Experimental Examples 1 and 2

To a pressure vessel is charged distilled DMADMPAL (1.0 equivalent), a Raney® Nickel slurry available from Sigma-Aldrich, catalog number 510033 (W.R. Grace and Co. Raney® 2400, slurry in $H_2O$, active catalyst). The amount of catalyst utilized is about 10 to about 100 weight percent relative to the amount of DMADMPAL. The vessel is closed and flushed with $H_2$ for about 5 minutes with occasional stirring. The pressure in the vessel is increased to a pressure in the range of about 100 psi to about 1,000 psi and then heated to a temperature in the range of about 30° C. to about 150° C. The heating is continued for about 3 hours until the pressure does not drop. The reaction vessel is then cooled and the pressure is released before it is flushed with $N_2$ for about 10 minutes. The solution is filtered and analyzed by $^1$H NMR.

Exemplary Procedure for the Hydrogenation of Crude DMADMPAL

Experimental Examples 3, 4 and 5

To a pressure vessel is charged crude DMADMPAL (1.0 equivalent), a Raney® Nickel slurry available from Sigma-Aldrich, catalog number 510033 (W.R. Grace and Co. Raney® 2400, slurry in $H_2O$, active catalyst). The amount of catalyst utilized is about 10 to about 100 weight percent relative to the amount of DMADMPAL. The vessel is closed and flushed with $H_2$ for about 5 minutes with occasional stirring. The pressure in the vessel is increased to a pressure in the range of about 100 psi to about 1,000 psi and then heated to a temperature in the range of about 30° C. to about 150° C. The heating is continued for about 3 hours until the pressure does not drop. The reaction vessel is then cooled and the pressure is released before it is flushed with $N_2$ for about 10 minutes. The crude solution is filtered and analyzed by $^1$H NMR.

While in accordance with the patent statutes the best mode and certain embodiments of the invention have been set forth, the scope of the invention is not limited thereto, but rather by the scope of the attached. As such, other variants within the spirit and scope of this invention are possible and will present themselves to those skilled in the art.

What is claimed is:

1. A method for producing an aminoalcohol from an aminoaldehyde, the method comprising the steps of:

(i) subjecting a composition comprising an aminoaldehyde according to Formula (I) below to a hydrogenation reaction by combining the aminoaldehyde with hydrogen and a hydrogenation catalyst to yield a corresponding aminoalcohol, wherein the aminoaldehyde is not protonated or neutralized during the reaction:

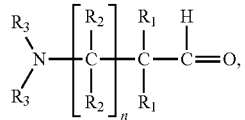

where each $R_1$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_1$ substituents and the carbon atom to which they are attached can form a saturated or unsaturated $C_3$ to $C_{20}$ cyclic group, heterocyclic group or carbocyclic group; where each $R_2$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_2$ substituents and the carbon atom to which they are attached can form a saturated or unsaturated $C_3$ to $C_{20}$ cyclic group, heterocyclic group or carbocyclic group; where one $R_1$ substituent and one $R_2$ substituent and the carbon atoms to which they are attached can form a saturated $C_3$ to $C_{20}$ cyclic group or a saturated $C_3$ to $C_{20}$ heterocyclic group, wherein the remaining $R_1$ substituent and $R_2$ substituent either form a second cyclic structure as defined above or wherein the remaining $R_1$ substituent and $R_2$ substituent are individually substituted with a group listed above; where each $R_3$ is independently selected from hydrogen, linear or branched $C_1$ to $C_{30}$ alkyl groups, linear or branched $C_1$ to $C_{30}$ alkyl groups that contain one or more heteroatoms, linear or branched $C_2$ to $C_{30}$ alkenyl groups, linear or branched $C_2$ to $C_{30}$ alkenyl groups that contain one or more heteroatoms, linear or branched $C_2$ to $C_{30}$ alkynyl groups, linear or branched $C_2$ to $C_{30}$ alkynyl groups that contain one or more heteroatoms, $C_4$ to $C_{20}$ aryl groups, $C_4$ to $C_{20}$ aryl groups that contain one or more heteroatoms, $C_4$ to $C_{20}$ cycloalkyl groups, $C_4$ to $C_{20}$ cycloalkyl groups that contain one or more heteroatoms, $C_4$ to $C_{20}$ heterocyclic groups, or where both $R_3$ substituents and the nitrogen atom to which they are attached can form a substituted or unsubstituted, saturated or unsaturated $C_2$ to $C_{20}$ heterocyclic group or a substituted or unsubstituted, saturated or unsaturated $C_2$ to $C_{20}$ heterocyclic group having two or more heteroatoms, where said heteroatoms are optionally substituted; and where n is equal to an integer in the range of 1 to 30; and (ii) collecting the aminoalcohol.

2. The method of claim 1, wherein each $R_1$ is independently selected from hydrogen, or linear or branched $C_1$ to $C_6$ alkyl groups; each $R_2$ is independently selected from hydrogen, or linear or branched $C_1$ to $C_6$ alkyl groups; and each $R_3$ is independently selected from hydrogen, linear or branched $C_1$ to $C_{15}$ alkyl groups, linear or branched $C_1$ to $C_{15}$ alkyl groups that contain one or more heteroatoms, linear or branched $C_2$ to $C_{15}$ alkenyl groups, linear or branched $C_2$ to $C_{15}$ alkenyl groups that contain one or more heteroatoms, linear or branched $C_2$ to $C_{15}$ alkynyl groups, linear or branched $C_2$ to $C_{15}$ alkynyl groups that contain one or more heteroatoms, $C_4$ to $C_{10}$ aryl groups, $C_4$ to $C_{10}$ aryl groups that contain one or more heteroatoms, $C_4$ to $C_{10}$ cycloalkyl groups, $C_4$ to $C_{10}$ cycloalkyl groups that contain one or more heteroatoms, or $C_4$ to $C_{10}$ heterocyclic groups.

3. The method of claim 1, wherein each $R_1$ is a methyl group, each $R_2$ is a hydrogen; each $R_3$ is selected from a linear or branched $C_1$ to $C_8$ alkyl groups; and wherein n is equal to an integer from 1 to 5.

4. The method of claim 1, wherein the amount of hydrogenation catalyst utilized in Step (i) is in the range of 0.0001 to 0.8 weight equivalents of hydrogenation catalyst per 1 weight equivalent of aminoaldehyde.

5. The method of claim 1, wherein Step (i) is conducted at a pressure in the range of 6.89 kPa to 68.94 MPa (1 psi to 10,000 psi).

6. The method of claim 1, wherein said aminoaldehyde is 3-dimethylamino-2,2-dimethyl-1-propanal.

7. A method for producing an aminoalcohol from an aminoaldehyde, the method comprising the steps of:
(A) combining an aminoaldehyde according to Formula (I) below with less than a stoichiometric amount of an acid to form an aminoaldehyde composition comprising an aminoaldehyde salt:

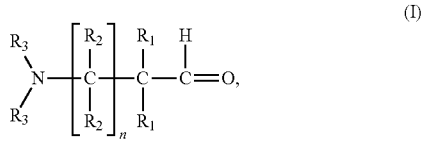

where each $R_1$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_1$ substituents and the carbon atom to which they are attached can form a saturated or unsaturated $C_3$ to $C_{20}$ cyclic group, heterocyclic group or carbocyclic group; where each $R_2$ is independently selected from hydrogen, linear or branched $C_1$ to $C_{30}$ alkyl groups, $C_3$ to $C_{20}$ cycloalkyl groups, saturated $C_2$ to $C_{20}$ heterocyclic groups, linear or branched $C_1$ to $C_{30}$ alkyl groups that can contain one or more of, or any mixture thereof, either $C_3$ to $C_{20}$ cycloalkyl groups or saturated $C_2$ to $C_{20}$ heterocyclic groups, or where both $R_2$ substituents and the carbon atom to which they are attached can form a saturated or unsaturated $C_3$ to $C_{20}$ cyclic group, heterocyclic group or carbocyclic group; where one $R_1$ substituent and one $R_2$ substituent and the carbon atoms to which they are attached can form a saturated $C_3$ to $C_{20}$ cyclic group or a saturated $C_3$ to $C_{20}$ heterocyclic group, wherein the remaining $R_1$ substituent and $R_2$ substituent either form a second cyclic structure as defined above or wherein the remaining $R_1$ substituent and $R_2$ substituent are individually substituted with a group listed above; where each $R_3$ is independently selected from hydrogen, linear or branched $C_1$ to $C_{30}$ alkyl groups, linear or branched $C_1$ to $C_{30}$ alkyl groups that contain one or more heteroatoms, linear or branched $C_2$ to $C_{30}$ alkenyl groups, linear or branched $C_2$ to $C_{30}$ alkenyl groups that contain one or more heteroatoms, linear or branched $C_2$ to $C_{30}$ alkynyl groups, linear or branched $C_2$ to $C_{30}$ alkynyl groups that contain one or more heteroatoms, $C_4$ to $C_{20}$ aryl groups, $C_4$ to $C_{20}$ aryl groups that contain one or more heteroatoms, $C_4$ to $C_{20}$ cycloalkyl groups, $C_4$ to $C_{20}$ cycloalkyl groups that contain one or more heteroatoms, $C_4$ to $C_{20}$ heterocyclic groups, or where both $R_3$ substituents and the nitrogen atom to which they are attached can form a substituted or unsubstituted, saturated or unsaturated $C_2$ to $C_{20}$ heterocyclic group or a substituted or unsubstituted, saturated or unsaturated $C_2$ to $C_{20}$ heterocyclic group having two or more heteroatoms, where said heteroatoms are optionally substituted; and where n is equal to an integer in the range of 1 to about 30; and
(B) subjecting the aminoaldehyde composition to a hydrogenation reaction by combining the aminoaldehyde composition with hydrogen and a hydrogenation catalyst to yield a corresponding aminoalcohol composition comprising an aminoalcohol salt.

8. The method of claim 7, wherein each $R_1$ is independently selected from hydrogen, or linear or branched $C_1$ to $C_6$ alkyl groups; each $R_2$ is independently selected from hydrogen, or linear or branched $C_1$ to $C_6$ alkyl groups; and each $R_3$ is independently selected from hydrogen, linear or branched $C_1$ to $C_{15}$ alkyl groups, linear or branched $C_1$ to $C_{15}$ alkyl groups that contain one or more heteroatoms, linear or branched $C_2$ to $C_{15}$ alkenyl groups, linear or branched $C_2$ to $C_{15}$ alkenyl groups that contain one or more heteroatoms, linear or branched $C_2$ to $C_{15}$ alkynyl groups, linear or branched $C_2$ to $C_{15}$ alkynyl groups that contain one or more heteroatoms, $C_4$ to $C_{10}$ aryl groups, $C_4$ to $C_{10}$ aryl groups that contain one or more heteroatoms, $C_4$ to $C_{10}$ cycloalkyl groups, $C_4$ to $C_{10}$ cycloalkyl groups that contain one or more heteroatoms, or $C_4$ to $C_{10}$ heterocyclic groups.

9. The method of claim 7, wherein each $R_1$ is a methyl group, each $R_2$ is a hydrogen; each $R_3$ is selected from a linear or branched $C_1$ to $C_8$ alkyl groups; and wherein n is equal to an integer from 1 to 5.

10. The method of claim 7, wherein the amount of acid utilized in Step (A) is less than 0.9 molar equivalents for every 1 molar equivalent of aminoaldehyde.

11. The method of claim 7, wherein the amount of hydrogenation catalyst utilized in Step (B) is in the range of 0.0001 to 0.8 weight equivalents of catalyst per 1 weight equivalent of aminoaldehyde.

12. The method of claim 7, wherein each of Step (A) or Step (B) is independently conducted at a pressure in the range of 6.89 kPa to 68.94 MPa (1 psi to 10,000 psi).

13. The method of claim 7, wherein each of Step (A) or Step (B) is independently conducted at a temperature in the range of 0° C. to 300° C.

14. The method of claim 1, wherein the hydrogenation catalyst is a nickel-aluminum binary catalyst.

15. The method of claim 1, wherein the aminoalcohol is 3-dimethylamino-2,2-dimethyl-1-propanol.

16. The method of claim 7, wherein the hydrogenation catalyst is a nickel-aluminum binary catalyst.

17. The method of claim 7, further comprising:
(C) neutralizing the aminoalcohol composition obtained in step (B) with a base to obtain a free aminoalcohol.

18. The method of claim 17, further comprising:
(D) collecting the free aminoalcohol of step (C).

19. The method of claim 18, wherein the free aminoalcohol is 3-dimethylamino-2,2-dimethyl-1-propanol.

* * * * *